United States Patent
Jeffrey

(10) Patent No.: US 9,797,344 B2
(45) Date of Patent: Oct. 24, 2017

(54) SYSTEM AND METHOD FOR DIAGNOSING A DUAL PATH PURGE SYSTEM USING A HYDROCARBON SENSOR AND FOR DIAGNOSING A HYDROCARBON SENSOR IN A SINGLE PATH PURGE SYSTEM OR A DUAL PATH PURGE SYSTEM

(71) Applicant: GM Global Technology Operations LLC, Detroit, MI (US)

(72) Inventor: Scott Jeffrey, Hartland, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 360 days.

(21) Appl. No.: 14/539,108

(22) Filed: Nov. 12, 2014

(65) Prior Publication Data

US 2016/0061153 A1   Mar. 3, 2016

Related U.S. Application Data

(60) Provisional application No. 62/043,741, filed on Aug. 29, 2014.

(51) Int. Cl.
  *F02M 25/08* (2006.01)
  *G01N 33/00* (2006.01)
  (Continued)

(52) U.S. Cl.
  CPC .... *F02M 25/0809* (2013.01); *F02M 25/0836* (2013.01); *G01N 33/0047* (2013.01);
  (Continued)

(58) Field of Classification Search
  CPC ........... F02M 25/0809; F02M 25/0836; G01N 33/0047; F02D 13/06; F02D 13/0219; F02D 2200/0406; F02D 2200/703; F02D 41/003
  See application file for complete search history.

(56) References Cited

U.S. PATENT DOCUMENTS 5,125,385 A  *  6/1992  Frinzel ............... F02M 25/0809
                                                        123/520
5,251,477 A  *  10/1993  Nakashima ........ F02M 25/0809
                                                        73/114.39

(Continued)

FOREIGN PATENT DOCUMENTS

| DE | 102010012913 A1 | 9/2011 |
| DE | 102011104424 A1 | 12/2012 |
| JP | 2013-185528 A | 9/2013 |

OTHER PUBLICATIONS

U.S. Appl. No. 14/539,187, filed Nov. 12, 2014, Swartz et al.
U.S. Appl. No. 14/539,308, filed Nov. 12, 2014, Jeffrey.
U.S. Appl. No. 14/539,108, filed Nov. 12, 2014, Jeffrey.

*Primary Examiner* — David Hamaoui

(57) ABSTRACT

A system according to the present disclosure includes a valve control module, a purge fraction module, and a diagnostic module. The valve control module opens a purge valve in an evaporative emissions system to allow purge vapor to flow to an intake system of an engine. The purge fraction module determines first and second fractions of purge vapor delivered to the engine relative to a total amount of air and purge vapor delivered to the engine based on first and second inputs, respectively. The first input is from a hydrocarbon sensor disposed in the evaporative emissions system of the engine. The second input is from an oxygen sensor disposed in an exhaust system of the engine. The diagnostic module selectively diagnoses a fault in at least one of the evaporative emissions system and the hydrocarbon sensor based on the first and second purge fractions when the purge valve is open.

20 Claims, 3 Drawing Sheets

(51) Int. Cl.
*F02D 41/00* (2006.01)
*F02D 13/02* (2006.01)
*F02D 13/06* (2006.01)

(52) U.S. Cl.
CPC .......... *F02D 13/0219* (2013.01); *F02D 13/06* (2013.01); *F02D 41/003* (2013.01); *F02D 2200/0406* (2013.01); *F02D 2200/703* (2013.01)

(56) References Cited

U.S. PATENT DOCUMENTS

| | | | | |
|---|---|---|---|---|
| 5,251,592 A | * | 10/1993 | Seki | F02M 25/08 123/198 D |
| 5,327,776 A | * | 7/1994 | Yasui | F02M 25/0809 73/114.39 |
| 5,343,846 A | * | 9/1994 | Ogawa | F02D 41/0045 123/520 |
| 5,474,050 A | | 12/1995 | Cook et al. | |
| 5,529,047 A | * | 6/1996 | Aota | F02D 41/004 123/674 |
| 5,669,362 A | | 9/1997 | Shinohara et al. | |
| 6,276,343 B1 | | 8/2001 | Kawamura et al. | |
| 6,321,728 B1 | * | 11/2001 | Ohkuma | F02M 25/0809 123/520 |
| 6,499,476 B1 | | 12/2002 | Reddy | |
| 6,739,177 B2 | * | 5/2004 | Sato | F02D 41/0037 73/114.71 |
| 6,874,485 B2 | * | 4/2005 | Fujimoto | F02D 41/0045 123/198 D |
| 8,122,758 B2 | | 2/2012 | Wang et al. | |
| 9,356,215 B2 | * | 5/2016 | Iriyama | F01N 5/025 |
| 2014/0144416 A1 | * | 5/2014 | Heinrich | F02D 41/0042 123/672 |
| 2015/0013437 A1 | | 1/2015 | Takakura | |
| 2015/0020780 A1 | * | 1/2015 | Takakura | F02M 25/0809 123/520 |
| 2015/0198123 A1 | * | 7/2015 | Pearce | B60K 15/03504 123/520 |

\* cited by examiner

_US 9,797,344 B2_

SYSTEM AND METHOD FOR DIAGNOSING A DUAL PATH PURGE SYSTEM USING A HYDROCARBON SENSOR AND FOR DIAGNOSING A HYDROCARBON SENSOR IN A SINGLE PATH PURGE SYSTEM OR A DUAL PATH PURGE SYSTEM

CROSS-REFERENCE TO RELATED APPLICATIONS

This application claims the benefit of U.S. Provisional Application No. 62/043,741, filed on Aug. 29, 2014. The disclosure of the above application is incorporated herein by reference in its entirety.

This application is related to U.S. patent application Ser. No. 14/539,187, which is filed on the same day as this application and claims the benefit of U.S. Provisional Application No. 62/043,724 filed on Aug. 29, 2014; and Ser. No. 14/539,308 filed on the same day as this application. The entire disclosures of the above applications are incorporated herein by reference.

FIELD

The present disclosure relates to internal combustion engines, and more specifically, to systems and methods for diagnosing a dual path purge system using a hydrocarbon sensor and for diagnosing a hydrocarbon sensor in a single path purge system or a dual path purge system.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Evaporative emissions systems collect fuel vapor from a fuel tank and deliver the fuel vapor to an intake system for combustion in an engine. An evaporative emissions system typically includes a canister that absorbs fuel vapor from the fuel tank and a purge valve that controls the flow of fuel vapor from the canister to the intake system. Single path purge systems include a single path extending from the purge valve to the intake system. Dual path purge systems include two paths extending from the purge valve to the intake system.

Dual path purge systems are typically used for engine systems that include a boost device, such as a turbocharger, which pressurizes intake air provided to the engine. In these applications, dual path systems typically include a boosted path that provides fuel vapor to the intake system upstream from the boost device and a non-boosted path that provides fuel vapor to the intake system downstream from the boost device. In various dual path purge systems, the boosted path includes a jet pump that draws fuel vapor through the first path when the boost device is providing boost. The jet pump includes a first inlet in communication with the canister, a second inlet in communication with a location in the intake system downstream from the boost device, and an outlet in communication with the intake system upstream from the boost device.

SUMMARY

A system according to the present disclosure includes a valve control module, a purge fraction module, and a diagnostic module. The valve control module opens a purge valve in an evaporative emissions system to allow purge vapor to flow to an intake system of an engine. The purge fraction module determines first and second fractions of purge vapor delivered to the engine relative to a total amount of air and purge vapor delivered to the engine based on first and second inputs, respectively. The first input is from a hydrocarbon sensor disposed in the evaporative emissions system of the engine. The second input is from an oxygen sensor disposed in an exhaust system of the engine. The diagnostic module selectively diagnoses a fault in at least one of the evaporative emissions system and the hydrocarbon sensor based on the first and second purge fractions when the purge valve is open.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

An engine control system typically controls a purge valve in an evaporative emissions system to yield a desired amount of flow from a canister in the evaporative emissions system to an intake system. Fuel vapor flowing from the canister to the intake system through the purge valve may be referred to as purge vapor. An engine control system may control the purge valve to achieve a desired amount of purge flow using closed-loop control with an actual purge fraction as feedback. A purge fraction is a fraction of purge vapor delivered to an engine relative to a total amount of purge vapor and air delivered to the engine. In one example, the actual purge fraction is determined based on an input from an oxygen sensor disposed in an exhaust system of the engine.

On occasion, a line extending from the canister to the intake system may become disconnected from the intake system. Thus, a diagnostic system may perform leak checks to identify such disconnections in an evaporative emissions system. However, the leak checks performed by conventional diagnostic systems may be inadequate to identify certain disconnections in a dual path purge system, such as a purge line in the boosted path disconnecting from the intake system.

A system and method according to the present disclosure identifies these types of disconnections using a hydrocarbon sensor disposed in the evaporative emissions system. When the purge valve is open, the system and method determines a first purge fraction based on an input from the hydrocarbon sensor and determines a second purge fraction based on an input from an oxygen sensor disposed in an exhaust system of the engine. The system and method may diagnose a disconnection when the first purge fraction is greater than the second purge fraction by a predetermined amount.

The system and method may also diagnose a fault in a hydrocarbon sensor in a single path purge system or a dual path purge system based on a difference between the first and second purge fractions. For example, the system and method may diagnose a fault in the hydrocarbon sensor when the difference between the first and second purge fractions is greater than a predetermined value. The system and method may diagnose a fault in a hydrocarbon sensor in a dual path purge system when purge vapor is flowing through the non-boosted path.

Figure 1:
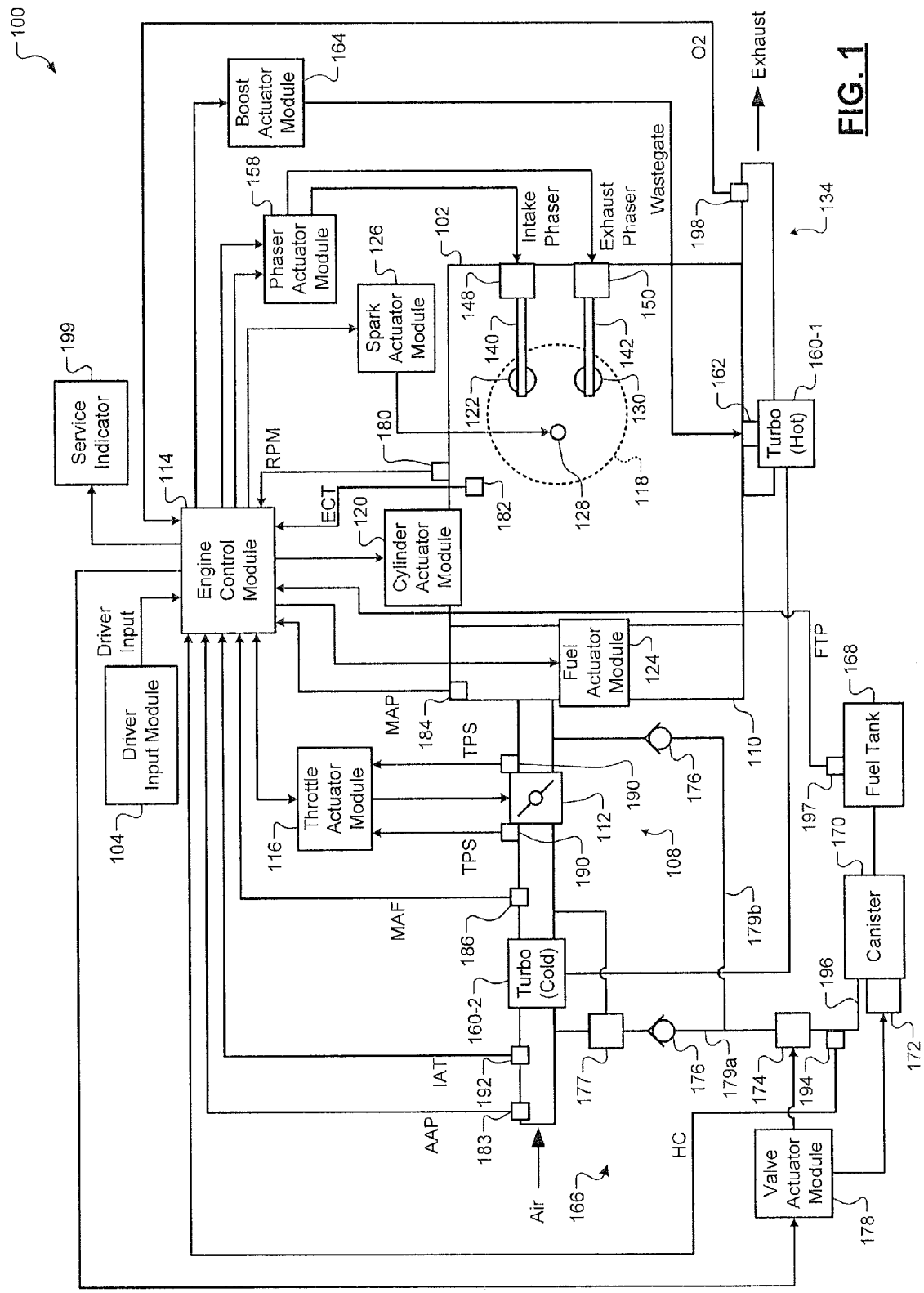
FIG. 1 is a functional block diagram of an example engine system according to the principles of the present disclosure.

Referring to FIG. 1, an engine system 100 includes an engine 102 that combusts an air/fuel mixture to produce drive torque for a vehicle based on driver input from a driver input module 104. The driver input may be based on a position of an accelerator pedal. The driver input may also be based on a cruise control system, which may be an adaptive cruise control system that varies vehicle speed to maintain a predetermined following distance.

Air is drawn into the engine 102 through an intake system 108. The intake system 108 includes an intake manifold 110 and a throttle valve 112. For example only, the throttle valve 112 may include a butterfly valve having a rotatable blade. An engine control module (ECM) 114 controls a throttle actuator module 116, which regulates opening of the throttle valve 112 to control the amount of air drawn into the intake manifold 110.

Air from the intake manifold 110 is drawn into cylinders of the engine 102. While the engine 102 may include multiple cylinders, for illustration purposes a single representative cylinder 118 is shown. For example only, the engine 102 may include 2, 3, 4, 5, 6, 8, 10, and/or 12 cylinders. The ECM 114 may instruct a cylinder actuator module 120 to selectively deactivate some of the cylinders, which may improve fuel economy under certain engine operating conditions.

The engine 102 may operate using a four-stroke cycle. The four strokes, described below, are named the intake stroke, the compression stroke, the combustion stroke, and the exhaust stroke. During each revolution of a crankshaft (not shown), two of the four strokes occur within the cylinder 118. Therefore, two crankshaft revolutions are necessary for the cylinder 118 to experience all four of the strokes.

During the intake stroke, air from the intake manifold 110 is drawn into the cylinder 118 through an intake valve 122. The ECM 114 controls a fuel actuator module 124, which regulates fuel injection to achieve a desired air/fuel ratio. Fuel may be injected into the intake manifold 110 at a central location or at multiple locations, such as near the intake valve 122 of each of the cylinders. In various implementations, fuel may be injected directly into the cylinders or into mixing chambers associated with the cylinders. The fuel actuator module 124 may halt injection of fuel to cylinders that are deactivated.

The injected fuel mixes with air and creates an air/fuel mixture in the cylinder 118. During the compression stroke, a piston (not shown) within the cylinder 118 compresses the air/fuel mixture. The engine 102 may be a compression-ignition engine, in which case compression in the cylinder 118 ignites the air/fuel mixture. Alternatively, the engine 102 may be a spark-ignition engine, in which case a spark actuator module 126 energizes a spark plug 128 in the cylinder 118 based on a signal from the ECM 114, which ignites the air/fuel mixture. The timing of the spark may be specified relative to the time when the piston is at its topmost position, referred to as top dead center (TDC).

The spark actuator module 126 may be controlled by a timing signal specifying how far before or after TDC to generate the spark. Because piston position is directly related to crankshaft rotation, operation of the spark actuator module 126 may be synchronized with crankshaft angle. In various implementations, the spark actuator module 126 may halt provision of spark to deactivated cylinders.

Generating the spark may be referred to as a firing event. The spark actuator module 126 may have the ability to vary the timing of the spark for each firing event. The spark actuator module 126 may even be capable of varying the spark timing for a next firing event when the spark timing signal is changed between a last firing event and the next firing event. In various implementations, the engine 102 may include multiple cylinders and the spark actuator module 126 may vary the spark timing relative to TDC by the same amount for all cylinders in the engine 102.

During the combustion stroke, the combustion of the air/fuel mixture drives the piston down, thereby driving the crankshaft. The combustion stroke may be defined as the time between the piston reaching TDC and the time at which the piston returns to bottom dead center (BDC). During the exhaust stroke, the piston begins moving up from BDC and expels the byproducts of combustion through an exhaust valve 130. The byproducts of combustion are exhausted from the vehicle via an exhaust system 134.

The intake valve 122 may be controlled by an intake camshaft 140, while the exhaust valve 130 may be controlled by an exhaust camshaft 142. In various implementations, multiple intake camshafts (including the intake camshaft 140) may control multiple intake valves (including the intake valve 122) for the cylinder 118 and/or may control the intake valves (including the intake valve 122) of multiple banks of cylinders (including the cylinder 118). Similarly, multiple exhaust camshafts (including the exhaust camshaft 142) may control multiple exhaust valves for the cylinder 118 and/or may control exhaust valves (including the exhaust valve 130) for multiple banks of cylinders (including the cylinder 118).

The cylinder actuator module 120 may deactivate the cylinder 118 by disabling opening of the intake valve 122 and/or the exhaust valve 130. In various implementations, the intake valve 122 and/or the exhaust valve 130 may be controlled by devices other than camshafts, such as electromagnetic or electrohydraulic actuators.

The time at which the intake valve 122 is opened may be varied with respect to piston TDC by an intake cam phaser 148. The time at which the exhaust valve 130 is opened may be varied with respect to piston TDC by an exhaust cam phaser 150. A phaser actuator module 158 may control the intake cam phaser 148 and the exhaust cam phaser 150 based on signals from the ECM 114. When implemented, variable valve lift may also be controlled by the phaser actuator module 158.

The engine system 100 may include a boost device that provides pressurized air to the intake manifold 110. For example, FIG. 1 shows a turbocharger including a hot turbine 160-1 that is powered by hot exhaust gases flowing through the exhaust system 134. The turbocharger also includes a cold air compressor 160-2, driven by the turbine 160-1, that compresses air leading into the throttle valve 112. In various implementations, a supercharger (not shown), driven by the crankshaft, may compress air from the throttle valve 112 and deliver the compressed air to the intake manifold 110.

A wastegate 162 may allow exhaust to bypass the turbine 160-1, thereby reducing the boost (the amount of intake air compression) of the turbocharger. The ECM 114 may control the turbocharger via a boost actuator module 164. The boost actuator module 164 may modulate the boost of the turbocharger by controlling the position of the wastegate 162. In various implementations, multiple turbochargers may be controlled by the boost actuator module 164. The turbocharger may have variable geometry, which may be controlled by the boost actuator module 164.

An intercooler (not shown) may dissipate some of the heat contained in the compressed air charge, which is generated as the air is compressed. The compressed air charge may also have absorbed heat from components of the exhaust system 134. Although shown separated for purposes of illustration, the turbine 160-1 and the compressor 160-2 may be attached to each other, placing intake air in close proximity to hot exhaust.

An evaporative emissions (EVAP) system 166 collects fuel vapor from a fuel tank 168 and delivers the fuel vapor to the intake system 108 for combustion in the engine 102. The EVAP system 166 includes a canister 170, a vent valve 172, a purge valve 174, check valves 176, and a jet pump 177. The canister 170 adsorbs fuel from the fuel tank 168. The vent valve 172 allows atmospheric air to enter the canister 170 when the vent valve 172 is open. The purge valve 174 allows fuel vapor to flow from the canister 170 to the intake system 108 when the purge valve 174 is open. The check valves 176 prevent flow from the intake system 108 to the canister 170. The ECM 114 controls a valve actuator module 178, which regulates the positions of the vent valve 172 and the purge valve 174. The ECM 114 may open the vent valve 172 and the purge valve 174 to purge fuel vapor from the canister 170 to the intake system 108.

Fuel vapor flows from the canister 170 to the intake system 108 through a first flow path 179a or a second flow path 179b. When the boost device is operating (e.g., when the wastegate 162 is closed), the pressure at the outlet of the first flow path 179a is less than the pressure at the outlet of the second flow path 179b. Thus, fuel vapor flows from the canister 170 to the intake system 108 through the first flow path 179a. When the boost device is not operating (e.g., when the wastegate 162 is open), the pressure at the outlet of the first flow path 179a is greater than the pressure at the outlet of the second flow path 179b. Thus, fuel vapor flows from the canister 170 to the intake system 108 through the second flow path 179b. In this regard, the first flow path 179a may be referred to as the boosted path, and the second flow path 179b may be referred to as the non-boosted path.

When the boost device is operating, the pressure of intake air upstream from the compressor 160-2 is less than the pressure of intake air downstream from the compressor 160-2. The jet pump 177 utilizes this pressure difference to create a vacuum that draws fuel vapor from the canister 170 into the intake system 108. The fuel vapor flows through the jet pump 177 and enters the intake system 108 upstream from the compressor 160-2.

In various implementations, the EVAP system 166 may include a single flow path extending from the canister 170 to the intake system 108 at a location downstream from the throttle valve 112. For example, the first flow path 179a and the components disposed therein may be omitted. In turn, the second flow path 179b may be the only path for fuel vapor to flow from the canister 170 to the intake system 108.

The engine system 100 may measure the position of the crankshaft using a crankshaft position (CKP) sensor 180. The temperature of the engine coolant may be measured using an engine coolant temperature (ECT) sensor 182. The ECT sensor 182 may be located within the engine 102 or at other locations where the coolant is circulated, such as a radiator (not shown).

The pressure of ambient air being drawn into the engine 102 may be measured using an ambient air pressure (AAP) sensor 183. The pressure within the intake manifold 110 may be measured using a manifold absolute pressure (MAP) sensor 184. In various implementations, engine vacuum, which is the difference between the ambient air pressure and the intake manifold pressure, may be measured.

The mass flow rate of air flowing into the intake manifold 110 may be measured using a mass air flow (MAF) sensor 186. In various implementations, the MAF sensor 186 may be located in a housing that also includes the throttle valve 112. The throttle actuator module 116 may monitor the position of the throttle valve 112 using one or more throttle position sensors (TPS) 190. The temperature of ambient air being drawn into the engine 102 may be measured using an intake air temperature (IAT) sensor 192.

The concentration of hydrogen in air flowing through the purge valve 174 may be measured using a hydrocarbon (HC) sensor 194. The HC sensor 194 may be disposed in the EVAP system 166 upstream from the purge valve 174, for example, in a line 196 extending between the canister 170 and the purge valve 174. Alternatively, the HC sensor 194 may be located in the canister 170, in the purge valve 174, or at a location downstream from the purge valve 174 and upstream from the point where the first and second flow paths 179a and 179b split apart from each other.

The pressure within the fuel tank 168 may be measured using a fuel tank pressure (FTP) sensor 197. The concentration of oxygen in exhaust gas flowing through the exhaust system 134 may be measured using an oxygen (O2) sensor 198. The O2 sensor 198 may be located in the exhaust system 134 upstream from a catalytic converter (not shown). The ECM 114 may use signals from the sensors to make control decisions for the engine system 100.

The ECM 114 determines a first purge fraction and a second purge fraction based on inputs from the HC sensor 194 and the O2 sensor 198, respectively. The ECM 114 selectively diagnoses a fault in the EVAP system 166 and/or the HC sensor 194 based on the first and second purge fractions. For example, the ECM 114 may determine that the first flow path 179a disconnected from the intake system 108 when the first purge fraction is greater than the second purge fraction by a predetermined amount. The ECM 114 may set a diagnostic trouble code and/or activate a service indicator 199 when a fault is diagnosed. When activated, the service indicator 199 indicates that service is required using a visual message (e.g., text), an audible message (e.g., chime), and/or a tactile message (e.g., vibration).

Figure 2:
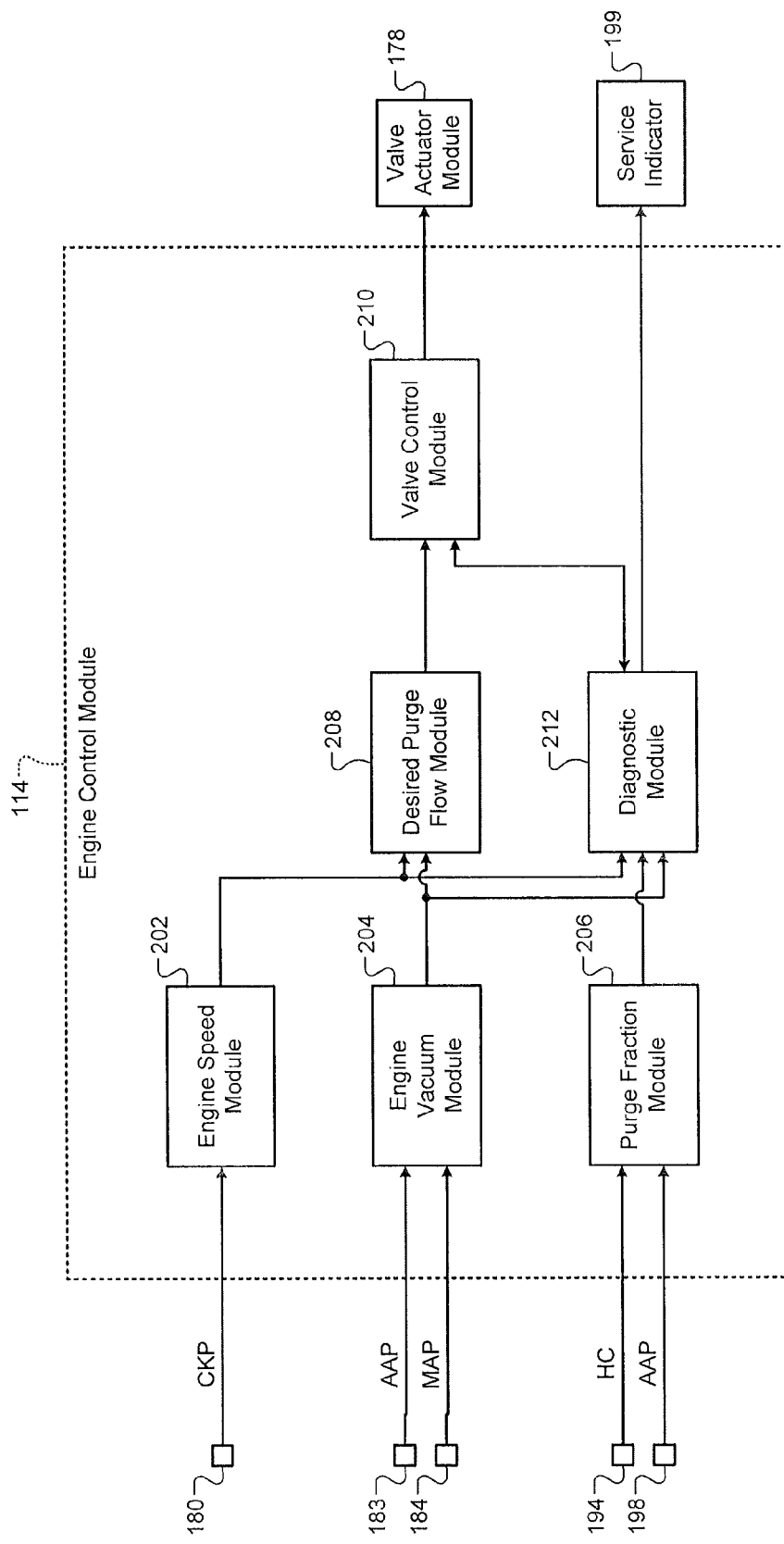
FIG. 2 is a functional block diagram of an example control system according to the principles of the present disclosure.

Referring to FIG. 2, an example implementation of the ECM 114 includes an engine speed module 202, an engine vacuum module 204, a purge fraction module 206, a desired purge flow module 208, a valve control module 210, and a diagnostic module 212. The engine speed module 202 determines engine speed. The engine speed module 202 may determine the engine speed based on the crankshaft position from the CKP sensor 180. For example, the engine speed module 202 may calculate the engine speed based on a period that elapses as the crankshaft completes one or more revolutions. The engine speed module 202 outputs the engine speed.

The engine vacuum module 204 determines engine vacuum. The engine vacuum module 204 may determine engine vacuum based on the atmospheric pressure from the AAP sensor 183 and the manifold pressure from the MAP sensor 184. The difference between the atmospheric pressure and the manifold pressure may be referred to as engine vacuum when the manifold pressure is less than the atmospheric pressure. The difference between the manifold pressure and the atmospheric pressure may be referred to as boost when the manifold pressure is greater than the atmospheric pressure. The engine vacuum module 204 outputs the engine vacuum (or boost).

The purge fraction module 206 determines a first purge fraction based on the hydrocarbon concentration from the HC sensor 194 and the mass flow rate of intake air from the MAF sensor 186. The purge fraction module 206 determines a second purge fraction based on the oxygen concentration from the O2 sensor 198 and the mass flow rate of intake air. The purge fraction module 206 may determine the first and second purge fractions when the purge valve 174 is open. For example, the purge fraction module 206 may determine the first and second purge fractions within a predetermined period (e.g., 1 minute to 8 minutes) after the purge valve 174 is opened.

The desired purge flow module 208 determines a desired purge flow. The desired purge flow module 208 may determine the desired purge flow based on the engine vacuum and/or the engine speed. The desired purge flow module 208 outputs the desired purge flow.

The valve control module 210 outputs a signal to the valve actuator module 178 to control the positions of the vent valve 172 and the purge valve 174. The valve control module 210 may output a duty cycle to control the position of the purge valve 174. The valve control module 210 may adjust the duty cycle to minimize a difference between the desired purge flow and an actual purge flow. The valve control module 210 may determine the actual purge flow based on the first purge fraction, the second purge fraction, and/or parameters that affect flow through the purge valve 174. These factors may include a pressure drop across the purge valve 174, the fuel tank temperature, and/or the voltage supplied to the purge valve 174.

The diagnostic module 212 selectively diagnoses a fault in the EVAP system 166 and/or the HC sensor 194 based on the first and second purge fractions. In one example, the diagnostic module 212 diagnoses a fault in the EVAP system 166 when the first purge fraction is greater than the second purge fraction by a predetermined amount. In another example, the diagnostic module 212 diagnoses a fault in the HC sensor 194 when a difference between the first and second flow purge fractions is greater than a predetermined value.

The diagnostic module 212 may activate the service indicator 199 when a fault is diagnosed in the EVAP system 166 and/or the HC sensor 194. In addition, when the diagnostic module 212 diagnoses a fault in the EVAP system 166 such as the first flow path 179a disconnecting from the intake system 108, the valve control module 210 may keep the purge valve 174 closed. Further, when a fault is diagnosed in the HC sensor 194, the valve control module 210 may control the purge valve 174 based on the second purge fraction and independent of the first purge fraction.

Figure 3:
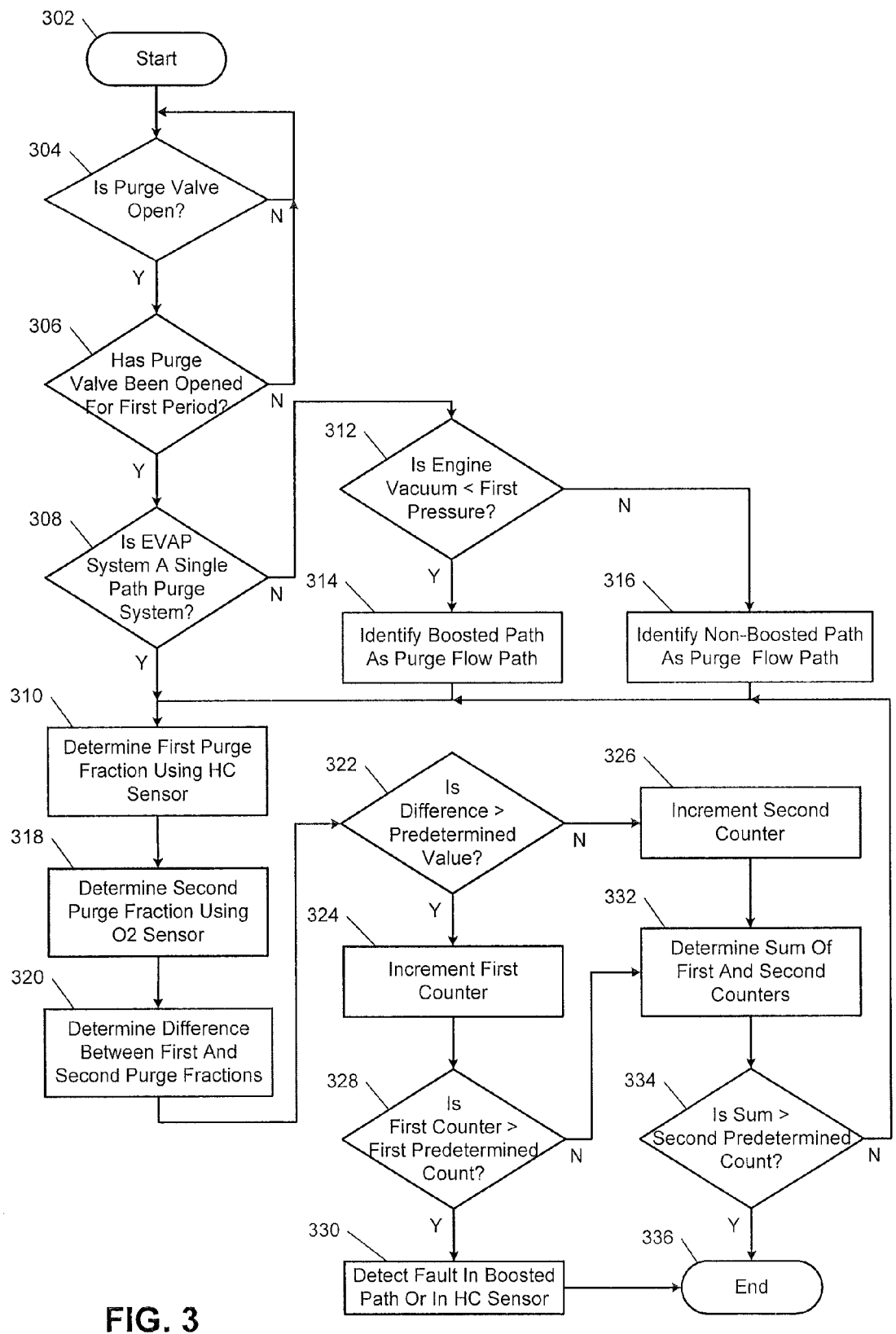
FIG. 3 is a flowchart illustrating an example control method according to the principles of the present disclosure.

Referring now to FIG. 3, a method of diagnosing a fault in the EVAP system 166 and/or the HC sensor 194 begins at 302. The method is described in the context of the modules included in the example implementation of the ECM 114 shown in FIG. 2 in order to further describe the functions performed by those modules. However, the particular modules that perform the steps of the method may be different than the description below and/or the method may be implemented apart from the modules of FIG. 2. For example, the method may be implemented by a single module.

At 304, the diagnostic module 212 determines whether the purge valve 174 is open. The diagnostic module 212 may determine whether the purge valve 174 is open based on an input from the valve control module 210. Alternatively, the diagnostic module 212 may determine whether the purge valve 174 is open based on the engine vacuum, as discussed in more detail below. If the purge valve 174 is open, the diagnostic module 212 continues at 306. Otherwise, the diagnostic module 212 continues to determine whether the purge valve 174 is open at 304.

At 306, the diagnostic module 212 determines whether the purge valve 174 has been opened for a first period. If the purge valve 174 has been opened for the first period, the diagnostic module 212 continues at 308. Otherwise, the diagnostic module 212 continues to determine whether the purge valve 174 has been opened for the first period at 306.

The first period may correspond to a delay from a time when the amount of purge vapor flowing through the purge valve 174 changes to a time when the second purge fraction determined based on an input from the O2 sensor 198 reflects the change. This delay may vary as a function of engine speed. Thus, in one example, the first period may have a first duration (e.g., 2 seconds) at idle speed and a second duration (e.g., milliseconds) at wide open throttle.

The first period may correspond to a delay from a time when the amount of purge vapor flowing through the purge valve 174 changes to a time when the second purge fraction reflects the change and stabilizes. In one example, the first period may end when the second purge fraction changes by less than a predetermined percentage (e.g., 6 percent) for a predetermined period. In another example, the first period may end when an integral gain used to adjust the position of the purge valve 174 based on the second purge fraction is within a predetermined range (e.g., 10 percent) for a predetermined period. The first period may vary from one minute to eight minutes, with the longest delay corresponding to a cold start when the canister 170 is fully loaded.

At 308, the diagnostic module 212 determines whether the EVAP system 166 is a single path purge system. If the EVAP system 166 is a single path purge system, the diagnostic module 212 continues at 310. Otherwise, the diagnostic module 212 continues at 312. If the EVAP system 166 is a single path purge system, the diagnostic module 212 may diagnose a disconnection in the single or non-boosted path (e.g., the second flow path 179b) independent of the input from the HC sensor 194. The diagnostic module 212 may then diagnose the HC sensor 194 based on the first and second purge fractions.

When diagnosing the non-boosted path independent of the input from the HC sensor 194, the diagnostic module 212 may first instruct the valve control module 210 to close the vent valve 172. Then, the diagnostic module 212 may monitor flow through the purge valve 174 for a predetermined period and determine a difference between fuel tank pressures measured by the FTP sensor 197 at the start and end of the predetermined period. If the difference is less than a predetermined value, indicating that the vacuum at the output of the purge valve 174 is insufficient, the diagnostic module 212 may diagnose a disconnection in the boosted path. The predetermined value may be selected from a lookup table based on the amount of flow through the purge valve 174.

At 312, the diagnostic module 212 determines whether the engine vacuum is less than a first pressure (e.g., 2 kilopascals (kPa)), which may be predetermined. If the engine vacuum is less than the first pressure, the diagnostic module 212 continues at 314 and identifies the boosted path (e.g., the first flow path 179*a*) as the purge vapor flow path (i.e., the path through which purge vapor is flowing). Otherwise, the diagnostic module 212 continues at 316 and identifies the non-boosted path (e.g., the second flow path 179*b*) as the purge vapor flow path.

In various implementations, when the engine vacuum is greater than or equal to the first pressure, the diagnostic module 212 may not immediately identify the non-boosted path as the purge vapor flow path. Instead, the diagnostic module 212 may first determine whether the engine vacuum is greater than a second pressure (e.g., −2 kPa), which may be predetermined. If the engine vacuum is greater than the second pressure, the diagnostic module 212 may determine that the purge valve 174 is closed and continue at 304. Otherwise, the diagnostic module 212 may continue at 316 and identify the non-boosted path as the purge vapor flow path.

If the boosted path is identified as the purge vapor flow path, the diagnostic module 212 may diagnose a fault in the EVAP system 166, such as a disconnection in the boosted path, based on the first and second purge fractions. If the non-boosted path is identified as the purge vapor flow path, the diagnostic module 212 may diagnose a disconnection in the non-boosted path independent of the input from the HC sensor 194 as described above. The diagnostic module 212 may then diagnose the HC sensor 194 based on the first and second purge fractions.

At 310, the purge fraction module 206 determines the first purge fraction based on the hydrocarbon concentration from the HC sensor 194. At 318, the purge fraction module 206 determines the second purge fraction based on the oxygen concentration from the O2 sensor 198. At 320, the diagnostic module 212 determines the difference between the first and second purge fractions.

At 322, the diagnostic module determines whether the difference between the first and second purge fractions is greater than a predetermined value. For example, if the diagnostic module 212 is diagnosing a disconnection in the boosted path (e.g., in the first flow path 179*a*), the diagnostic module may determine whether the first purge fraction is greater than the second purge fraction by a predetermined amount. In another example, if the diagnostic module 212 is diagnosing a fault in the HC sensor 194, the diagnostic module may determine whether an absolute value of the difference between the first and second purge fractions is greater than the predetermined value. If the difference between the first and second purge fractions is greater than a predetermined value, the diagnostic module 212 continues at 324. Otherwise, the diagnostic module 212 continues at 326.

At 324, the diagnostic module 212 increments a first counter. At 328, the diagnostic module determines whether the first counter is greater than a first predetermined count. If the first counter is greater than a first predetermined count, the diagnostic module 212 continues at 330 and diagnoses a fault in the one of the boosted path and the HC sensor 194 that is being diagnosed. Otherwise, the diagnostic module 212 continues at 332.

At 326, the diagnostic module 212 increments a second counter. At 332, the diagnostic module 212 determines a sum of the first and second counters, which represents the total number of times that the diagnostic module 212 has evaluated the difference between the first and second purge fractions. At 334, the diagnostic module 212 determines whether the sum is greater than a second predetermined count. If the sum is greater than a second predetermined count, the method ends at 336. Otherwise, the diagnostic module 212 continues at 310.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

In this application, including the definitions below, the term module may be replaced with the term circuit. The term module may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip.

The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this application may be partially or fully implemented by one or more computer programs executed by one or more processors. The computer programs include processor-executable instructions that are stored on at least one non-transitory tangible computer readable medium. The computer programs may also include and/or rely on stored data.

What is claimed is:

1. A system comprising:
  a valve control module that selectively opens a purge valve in an evaporative emissions system to allow purge vapor to flow to an intake system of an engine;
  a purge fraction module that:
    determines a first fraction of purge vapor delivered to the engine relative to a total amount of air and purge vapor delivered to the engine based on a first input from a hydrocarbon sensor disposed in the evaporative emissions system of the engine; and determines a second fraction of purge vapor delivered to the engine relative to the total amount of air and purge vapor delivered to the engine based on a second input from an oxygen sensor disposed in an exhaust system of the engine; and a diagnostic module that selectively diagnoses a fault in at least one of the evaporative emissions system and the hydrocarbon sensor based on the first and second purge fractions when the purge valve is open, wherein when a fault in at least one of the evaporative emissions system and the hydrocarbon sensor is diagnosed, at least one of:

the diagnostic module activates a service indicator; and the valve control module adjusts operation of the purge valve.

2. The system of claim 1 wherein the diagnostic module selectively diagnoses a fault in the at least one of the evaporative emissions system and the hydrocarbon sensor based on a difference between the first and second purge fractions within a predetermined period after the purge valve is opened.

3. The system of claim 1 wherein the evaporative emissions system includes a single path extending from the purge valve to the intake system.

4. The system of claim 3 wherein the diagnostic module diagnoses a fault in the hydrocarbon sensor when a difference between the first and second purge fractions is greater than a predetermined value.

5. The system of claim 1 wherein the evaporative emissions system includes a first path and a second path, the first path extending from the purge valve to a first location in the intake system upstream from a compressor, the second path extending from the purge valve to a second location in the intake system downstream from a throttle valve.

6. The system of claim 5 wherein the diagnostic module identifies one of the first path and the second path as a path through which purge vapor is flowing based on a difference between ambient air pressure and pressure within an intake manifold of the engine.

7. The system of claim 6 wherein the diagnostic module selectively diagnoses a fault in the evaporative emissions system based on the first and second purge fractions when purge vapor is flowing through the first path.

8. The system of claim 7 wherein the diagnostic module diagnoses a fault in the evaporative emissions system when the first purge fraction is greater than the second purge fraction by at least a predetermined amount.

9. The system of claim 6 wherein the diagnostic module selectively diagnoses a fault in the hydrocarbon sensor based on the first and second purge fractions when purge vapor is flowing through the second path.

10. The system of claim 9 wherein the diagnostic module diagnoses a fault in the hydrocarbon sensor when a difference between the first and second purge fractions is greater than a predetermined value.

11. A method comprising:

selectively opening a purge valve in an evaporative emissions system to allow purge vapor to flow to an intake system of an engine;

determining a first fraction of purge vapor delivered to the engine relative to a total amount of air and purge vapor delivered to the engine based on a first input from a hydrocarbon sensor disposed in the evaporative emissions system of the engine;

determining a second fraction of purge vapor delivered to the engine relative to the total amount of air and purge vapor delivered to the engine based on a second input from an oxygen sensor disposed in an exhaust system of the engine;

selectively diagnosing a fault in at least one of the evaporative emissions system and the hydrocarbon sensor based on the first and second purge fractions when the purge valve is open; and when a fault in at least one of the evaporative emissions system and the hydrocarbon sensor is diagnosed, at least one of:

activating a service indicator; and adjusting operation of the purge valve.

12. The method of claim 11 further comprising selectively diagnosing a fault in the at least one of the evaporative emissions system and the hydrocarbon sensor based on a difference between the first and second purge fractions within a predetermined period after the purge valve is opened.

13. The method of claim 11 wherein the evaporative emissions system includes a single path extending from the purge valve to the intake system.

14. The method of claim 13 further comprising diagnosing a fault in the hydrocarbon sensor when a difference between the first and second purge fractions is greater than a predetermined value.

15. The method of claim 11 wherein the evaporative emissions system includes a first path and a second path, the first path extending from the purge valve to a first location in the intake system upstream from a compressor, the second path extending from the purge valve to a second location in the intake system downstream from a throttle valve.

16. The method of claim 15 further comprising identifying one of the first path and the second path as a path through which purge vapor is flowing based on a difference between ambient air pressure and pressure within an intake manifold of the engine.

17. The method of claim 16 further comprising selectively diagnosing a fault in the evaporative emissions system based on the first and second purge fractions when purge vapor is flowing through the first path.

18. The method of claim 17 further comprising diagnosing a fault in the evaporative emissions system when the first purge fraction is greater than the second purge fraction by at least a predetermined amount.

19. The method of claim 16 further comprising selectively diagnosing a fault in the hydrocarbon sensor based on the first and second purge fractions when purge vapor is flowing through the second path.

20. The method of claim 19 further comprising diagnosing a fault in the hydrocarbon sensor when a difference between the first and second purge fractions is greater than a predetermined value.

* * * * *